United States Patent
Koyama et al.

(10) Patent No.: US 11,975,178 B2
(45) Date of Patent: May 7, 2024

(54) RESIN SYRINGE, PREFILLED SYRINGE, AND METHOD FOR PRODUCING RESIN SYRINGE

(71) Applicant: TERUMO KABUSHIKI KAISHA, Tokyo (JP)

(72) Inventors: Shingo Koyama, Shizuoka (JP); Kaori Enomoto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/198,193

(22) Filed: May 16, 2023

(65) Prior Publication Data

US 2023/0285679 A1    Sep. 14, 2023

Related U.S. Application Data

(63) Continuation of application No. 16/734,089, filed on Jan. 3, 2020, now abandoned, which is a continuation
(Continued)

(30) Foreign Application Priority Data

Jul. 4, 2017    (JP) .................................. 2017-131526

(51) Int. Cl.
*A61M 5/31*    (2006.01)
*A61L 2/07*    (2006.01)
(Continued)

(52) U.S. Cl.
CPC .......... *A61M 5/3129* (2013.01); *C08J 7/0427* (2020.01); *C09D 11/033* (2013.01);
(Continued)

(58) Field of Classification Search
CPC ........ A61M 5/3129; A61M 2005/3126; A61M 2005/3131; A61M 2207/00;
(Continued)

(56) References Cited

U.S. PATENT DOCUMENTS 4,275,729 A    6/1981   Silver et al.
4,724,508 A    2/1988   Macy
(Continued)

FOREIGN PATENT DOCUMENTS

EP    0 382 126 A2    8/1990
JP    H02-17078 A     1/1990
(Continued)

OTHER PUBLICATIONS

International Searching Authority, "International Search Report," issued in connection with International Patent Application No. PCT/JP2018/025353, dated Aug. 7, 2018.
(Continued)

*Primary Examiner* — Ariana Zimbouski
*Assistant Examiner* — Rachel T. Smith
(74) *Attorney, Agent, or Firm* — Foley & Lardner LLP (57) ABSTRACT

A resin syringe includes: a syringe body made of polyolefin, and a printing layer having a shape that extends in a band around an outer surface of the syringe body. The printing layer comprises components including chlorinated polypropylene having a degree of chlorination in a range of 15 to 30%, a colorant, and a filler. A plurality of recessed portions is formed in the outer surface of the syringe body on which the printing layer is printed and the recessed portions form a shape that extends in a band around the outer surface of the syringe body and that is entirely covered by the printing layer. Each of the recessed portions has a depth of 50 nm or more and less than 1 μm and a width of 50 nm or more and
(Continued)

less than 1 μm and is filled with at least one of the components of the printing layer.

20 Claims, 9 Drawing Sheets

Related U.S. Application Data of application No. PCT/JP2018/025353, filed on Jul. 4, 2018.

(51) Int. Cl.
*C08J 7/04* (2020.01)
*C09D 11/033* (2014.01)
*C09D 11/106* (2014.01)

(52) U.S. Cl.
CPC ............... *C09D 11/106* (2013.01); *A61L 2/07* (2013.01); *A61L 2202/24* (2013.01); *A61M 2005/3126* (2013.01); *A61M 2005/3131* (2013.01); *A61M 2207/00* (2013.01); *C08J 2345/00* (2013.01); *C08J 2423/12* (2013.01)

(58) Field of Classification Search
CPC .. A61M 2005/3104; A61M 2205/0238; A61M 2205/583; A61M 2205/60; A61M 5/28; C08J 7/0427; C08J 2345/00; C08J 2423/12; C08J 2323/12; C08J 2423/28; C09D 11/033; C09D 11/106; A61L 2/07; A61L 2202/24; B65B 3/003; B41M 1/40; B41M 5/0011; B41M 2205/12; B41M 2205/36; B41F 17/00–38; B41J 3/70733

See application file for complete search history.

(56) References Cited

U.S. PATENT DOCUMENTS

| 5,242,405 | A | * | 9/1993 | Howe | ................. | A61M 5/3129 |
| | | | | | | 604/218 |
| 6,444,317 | B1 | * | 9/2002 | Haruta | .................... | C08J 7/043 |
| | | | | | | 264/246 |
| 2002/0052577 | A1 | | 5/2002 | Shimazaki | | |
| 2004/0186437 | A1 | | 9/2004 | Frenette et al. | | |
| 2009/0177156 | A1 | * | 7/2009 | MacLean | ............ | A61M 5/3148 |
| | | | | | | 604/189 |
| 2017/0014431 | A1 | | 1/2017 | Yoshida et al. | | |
| 2018/0065323 | A1 | | 3/2018 | Condello et al. | | |
| 2019/0329537 | A1 | * | 10/2019 | Zama | ..................... | B32B 27/16 |

FOREIGN PATENT DOCUMENTS

| JP | H09-314793 | A | | 12/1997 | | |
| JP | 2006-057056 | A | | 3/2006 | | |
| JP | 2006-520639 | A | | 9/2006 | | |
| JP | 2007-276346 | A | | 10/2007 | | |
| JP | 2008-272162 | A | | 11/2008 | | |
| JP | 2014-185240 | A | | 10/2014 | | |
| WO | WO-2019000048 | A1 | * | 1/2019 | .............. | B41M 3/14 |

OTHER PUBLICATIONS

International Searching Authority, "Written Opinion," issued in connection with International Patent Application No. PCT/JP2018/025353, dated Aug. 7, 2018.

Extended European Search Report dated Nov. 25, 2020 in counterpart European Patent Application No. 18827619.0.

* cited by examiner

RESIN SYRINGE, PREFILLED SYRINGE, AND METHOD FOR PRODUCING RESIN SYRINGE

CROSS-REFERENCE TO RELATED APPLICATIONS

This is a Continuation of U.S. patent application Ser. No. 16/734,089, filed on Jan. 3, 2020, which is a bypass continuation of PCT Application No. PCT/JP2018/025353, filed on Jul. 4, 2018, which claims priority to Japanese Application No. 2017-131526, filed on Jul. 4, 2017. The contents of these applications are hereby incorporated by reference in their entireties.

BACKGROUND

The present disclosure relates to a resin syringe, a prefilled syringe, and a method for producing a resin syringe.

A prefillable syringe is a syringe that can be filled with a medicine to produce a prefilled syringe. Known prefillable syringes include a glass syringe and a resin syringe. The resin syringe is lighter than the glass syringe, is not broken even if dropped, and also has satisfactory dimensional precision, and thus has received attention as a prefillable syringe in recent years. A resin syringe is typically made of a cyclic olefin-based polymer or polyolefin such as polypropylene in order to secure transparency, but because these resins do not have a polar group, such a resin syringe is not suitable in a case in which graduation for indicating a capacity of a medicine, a medicine name, an expiration date, a logo, a lot number, and the like are directly printed and displayed. Further, when a printing layer printed on a surface of the prefillable syringe is peeled off, there is also considered a concern in that the printing layer is mixed as foreign matter when the medicine is filled. Therefore, on the resin syringe, in order to display graduation for indicating a capacity of a medicine, a medicine name, an expiration date, a logo, and a lot number, a label is adhered (for example, JP 2008-272162 A). Meanwhile, in a disposable resin syringe that is used for suctioning or preparing a medicine or the like in a hospital ward or the like, graduation for indicating an internal capacity is directly printed on an outer surface of a syringe body.

SUMMARY

However, in the prefilled syringe, depending on filled medicines, there is a case in which a dosage of a medicine has to be strictly controlled, and a problem arises in that the prefilled syringe lacks precision in graduation with a label. For this reason, a prefillable syringe made of a resin in which graduation or the like is printed on a syringe body is desired. In addition, in the disposable resin syringe in which graduation is directly printed, the outer surface of the syringe body may be rubbed, which may wear away the graduation during preparing the medicine, or the like.

In this regard, an object of certain embodiments of the present invention is to provide a resin syringe in which a printing layer, such as graduation, which is printed on an outer surface of a syringe body is unlikely to be peeled off, as well as a prefilled syringe, and a method for producing a resin syringe.

The present inventors have conducted intensive studies in order to solve the above-described problem. As a result, the present inventors have found that the above-described problem can be solved by providing a resin syringe including a syringe body made of polyolefin and a printing layer printed on at least a part of an outer surface of the syringe body, in which the printing layer has components including chlorinated polypropylene having a degree of chlorination in a range of 15 to 30%, a colorant, and a filler, the outer surface on which the printing layer is printed has a plurality of recessed portions, and each of the plurality of recessed portions has a depth of 50 nm or more and less than 1 µm and a width of 50 nm or more and less than 1 µm and is filled with at least one kind of the components of the printing layer.

According to certain embodiments of the present invention, it is possible to provide a resin syringe in which a printing layer printed on a syringe body is unlikely to be peeled off, a prefilled syringe, and a method for producing a resin syringe.

DETAILED DESCRIPTION

Hereinafter, embodiments of the present invention will be described. However, the present invention is not limited only to the following embodiments. Further, in the present specification, the expression "X to Y" indicating a range means "X or more and Y or less". In addition, operations and measurement of physical properties or the like are carried out under the conditions of at room temperature (20 to 25° C.)/relative humidity of 40 to 50% RH unless specifically noted.

[Resin Syringe]

FIGS. 1 to 4 are views provided for describing a prefilled syringe 1 or a resin syringe 10 according to an embodiment of the present invention. The prefilled syringe 1 according to an embodiment of the present invention includes, as described in outline with reference to FIG. 1, a resin syringe 10 provided with a syringe body 11, a medicine filled in an accommodating space 16 of the syringe body 11, a cap 20 (corresponding to a sealing member) sealing a distal end opening of the syringe body 11, a gasket 30 slidably disposed in the accommodating space 16 of the syringe body 11, and a plunger 40. The prefilled syringe is also called a cartridge in a case in which the prefilled syringe is used in a state of being integrated into an administration tool for administering a medicine filled in the syringe body.

Figure 4:
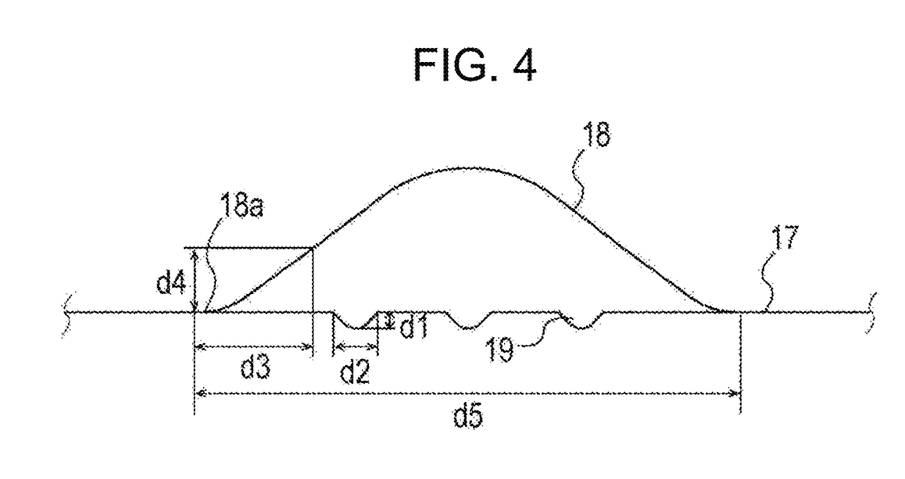
FIG. 4 is an enlarged view of the resin syringe and is a view illustrating the vicinity of a printing layer constituting the resin syringe.

The resin syringe 10 according to an embodiment of the present invention includes, as described with reference to FIG. 2, the syringe body 11 made of polyolefin and a printing layer 18 printed on at least a part of an outer surface 17 of the syringe body 11. The printing layer 18 has components including chlorinated polypropylene having a degree of chlorination in a range of 15 to 30%, a colorant, and a filler as illustrated in FIG. 4, and the outer surface 17 on which the printing layer 18 is printed has a plurality of recessed portions 19. Each of the plurality of recessed portions 19 has a depth d1 of 50 nm or more and less than 1 μm and a width d2 of 50 nm or more and less than 1 μm. Each of the plurality of recessed portions 19 is filled with at least one kind of the components of the printing layer 18. With such a configuration, it is possible to provide the resin syringe 10 in which the printing layer 18 printed on the syringe body is unlikely to be peeled off.

Figure 2:
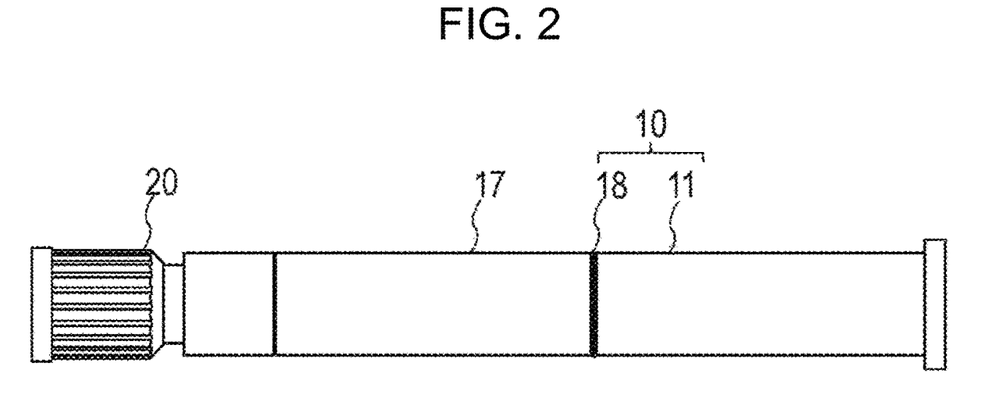
FIG. 2 is a view illustrating a resin syringe (prefillable syringe) according to an embodiment of the present invention.
Figure 3:
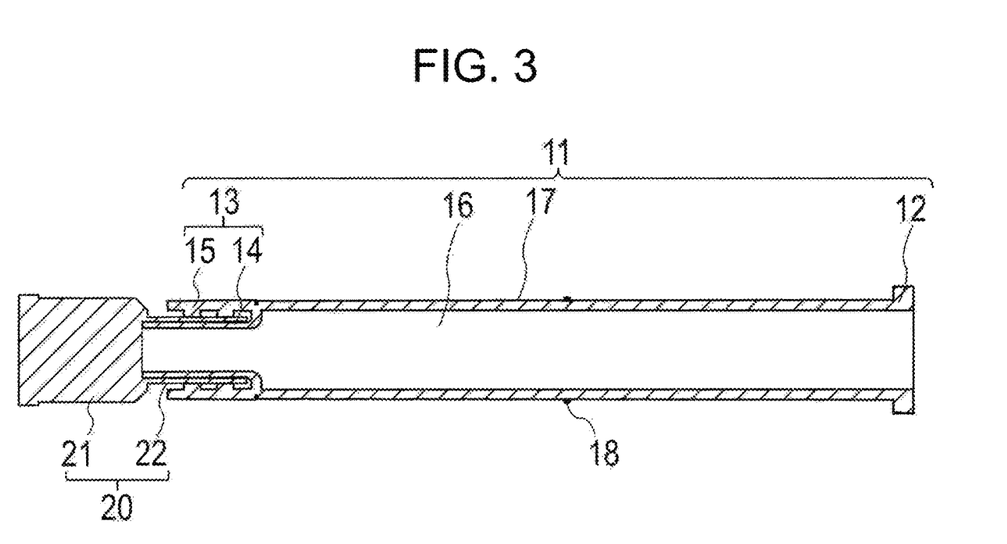
FIG. 3 is a cross-sectional view illustrating a state in which a center of the resin syringe of FIG. 2 is taken along an axial direction.

The resin syringe 10 includes, as illustrated in FIGS. 2 and 3, the syringe body 11 provided with a nozzle portion 13, which discharges a liquid such as a medicine, and the printing layer 18 provided on the outer surface of the syringe body 11. In this embodiment, the printing layer 18 is a graduation line indicating an internal capacity of the syringe body 11. As described above, depending on filled medicines, there is a case in which a dosage of a medicine has to be strictly controlled. However, in a case in which the graduation line is displayed by a label, by pasting the label itself, the graduation line is deviated from an intended position by about ±1 mm, and thus a dosage of a medicine cannot be strictly controlled. On the other hand, according to an embodiment of the present invention, because the printing layer 18 is formed directly on the outer surface 17 of the syringe body 11, deviation of the graduation line from an intended position can be extremely reduced within ±0.1 mm. Therefore, embodiments of the present invention are suitable for a syringe in which a dosage of a medicine has to be strictly controlled. As a matter of course, the printing layer 18 may indicate a medicine name, an expiration date, a logo, a lot number, a stop target position or retraction permissible position of the gasket 30, and the like.

The syringe body 11 includes, as illustrated in FIG. 3, a flange 12 provided on a proximal end of the syringe body 11, the nozzle portion 13 provided on a distal end of the syringe body 11, and the accommodating space 16 formed inside the syringe body 11. The syringe body 11 is, for example, formed in a hollow cylindrical shape. The flange 12 is formed to protrude from the outer surface of the proximal end portion of the syringe body 11 to the outside in a radial direction.

The nozzle portion 13 is provided to protrude in a distal direction. The nozzle portion 13 includes a discharge portion 14 discharging a liquid such as a medicine, and an attachment portion 15 provided to surround the outer periphery of the discharge portion 14. The nozzle portion 13 is formed in a double tube shape as illustrated in FIG. 3, and the inner tubular portion corresponds to the discharge portion 14 and the outer tubular portion corresponds to the attachment portion 15. The distal end of the discharge portion 14 is opened and forms a distal end opening of the syringe body 11.

The attachment portion 15 is a portion to which other medical instruments such as an injection needle (not illustrated) are attached, and in this embodiment, is integrally formed with the syringe body 11. As illustrated in FIG. 3, a female screw, which is screwed with a male screw of a mounting portion of other medical instruments such as an injection needle, is provided in the inner wall surface of the attachment portion 15. Incidentally, the attachment portion 15 can be configured as a separate part from other parts in the syringe body 11. Further, the attachment portion 15 may be omitted.

The accommodating space 16 corresponds to a cavity part that has a cylindrical shape and is provided radially inside the syringe body 11. A medicine or the like is filled in this accommodating space 16 and a gasket is further inserted so that the prefilled syringe 1 can be prepared. The accommodating space 16 is formed almost over the entire syringe body 11 along the axial direction of the syringe body 11.

The cap 20 includes a substantially cylindrical gripping portion 21 and a sealing portion 22 sealing the distal end opening of the syringe body 11, as illustrated in FIG. 3. In this embodiment, the sealing portion 22 is fitted to the outer periphery of the nozzle portion 13 of the syringe body 11 so that the cap 20 is attached to the syringe body 11. Further, the gripping portion 21 is disposed at the distal side in relation to the attachment portion 15 of the nozzle portion 13 and is a portion that is gripped by a user when the cap 20 is detached from the syringe body 11.

Figure 1:
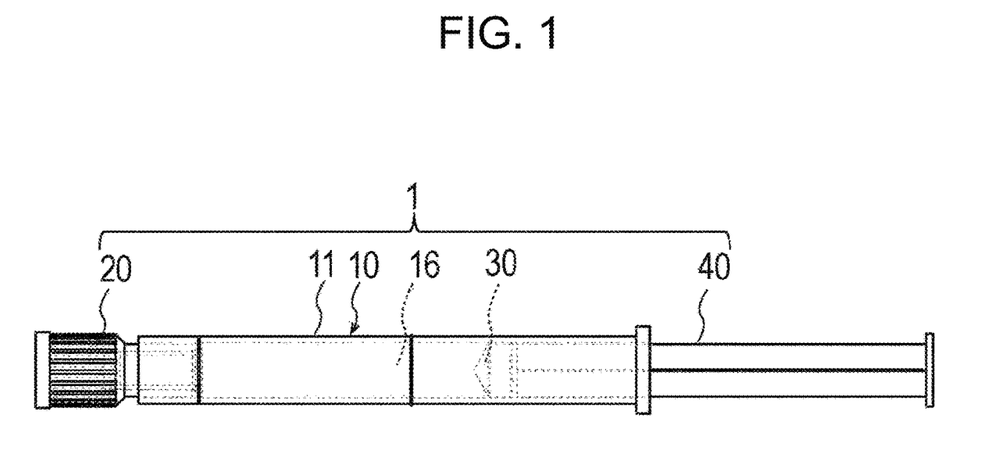
FIG. 1 is a view illustrating a prefilled syringe according to an embodiment of the present invention.

The syringe body and the sealing member may have a configuration different from the configurations illustrated in FIGS. 1 to 3. Specifically, instead of the nozzle portion 13 of the syringe body 11, a hollow puncture needle fixed to the distal end of the syringe body 11 may be provided. Further, instead of the cap 20 attached to the nozzle portion 13, a sealing member that is mounted on the distal portion of the syringe body to cover a puncture needle and seals a distal end opening of the puncture needle, may be used. In this case, the distal end opening of the puncture needle forms the distal end opening of the syringe body, and the distal portion of the puncture needle is inserted into the sealing member to seal the distal end opening of the puncture needle. Further, instead of the cap 20, a sealing member, which is fixed to the nozzle portion of the syringe body in a state of not being able to be detached, may be used. In this case, by inserting a medical instrument attached with a needle into the sealing member, the accommodating space and the outside are communicated with each other.

(Syringe Body Made of Polyolefin)

The syringe body 11 according to certain embodiments of the present invention is made of polyolefin. As compared with a glass syringe, the syringe made of polyolefin is lightweight, is not broken even if dropped, and also has satisfactory dimensional precision According to an embodiment of the present invention, the polyolefin constituting the syringe body 11 is a cyclo olefin polymer (COP), a cyclo olefin copolymer (COC), or polypropylene (PP). These polyolefins are desirable as a material forming the syringe body 11 in terms of transparency, steam sterilization property, and non-adsorbing property of a medicine, but they have a small polarity so that an adhesion force with the printing layer 18 that is printed tends to be weak. However, because the recessed portion 19 of the syringe body 11 is filled with at least one kind of the components of the printing layer 18, the printing layer 18 printed on the syringe body 11 is unlikely to be peeled off.

As the cyclo olefin polymer (COP), polymers obtained by ring-opening polymerization and hydrogenation of a cycloolefin-based monomer that is ring-opening polymerizable, such as norbornene or cyclotetradodecene, are suitably used. Further, as the cyclo olefin copolymer (COC), copolymers obtained by using norbornene and olefins such as ethylene as a raw material (addition copolymer of a norbornene-based monomer and α-olefin) and copolymers obtained by using tetracyclododecene and olefins such as ethylene as a raw material are suitably used.

As the cyclo olefin polymer (COP), for example, ZEONEX Resin manufactured by Zeon Corporation can be used. Further, as the cyclo olefin copolymer (COC), for example, APEL Resin manufactured by Mitsui Chemicals, Inc. can be used.

(Printing Layer and Outer Surface on which Printing Layer is Printed)

The resin syringe 10 of an embodiment of the present invention includes, as illustrated in FIG. 2, the syringe body 11 made of polyolefin and the printing layer 18 printed on at least a part of the outer surface 17 of the syringe body 11. The printing layer 18 has components including chlorinated polypropylene having a degree of chlorination in a range of 15 to 30%, a colorant, and a filler, as illustrated in FIG. 4, and the outer surface 17 on which the printing layer 18 is printed has a plurality of recessed portions 19. Each of the plurality of recessed portions 19 has a depth $d1$ of 50 nm or more and less than 1 μm and a width $d2$ of 50 nm or more and less than 1 μm. Each of the plurality of recessed portions 19 is filled with at least one kind of the components of the printing layer 18. With such a configuration, an anchor effect occurs between the printing layer 18 and the outer surface 17 and an adhesion strength is improved.

According to an embodiment of the present invention, the plurality of recessed portions 19 on the outer surface 17 on which the printing layer 18 is printed are configured by only recessed portions having the depth $d1$ and the width $d2$ in a range of 50 nm or more and less than 1 μm as illustrated in FIG. 4. Further, according to an embodiment of the present invention, each of the plurality of recessed portions 19 has the depth $d1$ in a range of 50 to 200 nm and the width $d2$ in a range of 100 to 500 nm. With such an embodiment, while the mechanical strength of the syringe body 11 is increased, an anchor effect between the printing layer 18 and the outer surface 17 can be increased.

Further, the outer surface 17 of the syringe body 11 itself is typically flat and smooth without portions considered as the recessed portions 19. Thus, according to an embodiment of the present invention, the outer surface 17 on which the printing layer 18 is printed has deeper recessed portions 19 than those of the outer surface 17 in a near-field region adjacent to the outer surface 17. Incidentally, the near-field region is an arbitrary region in the outer surface 17, which is adjacent to the printing layer 18 and has no printing layer 18 printed thereon, of the syringe body 11.

According to an embodiment of the present invention, at least one kind of the components of the printing layer 18 that is filled in each of the plurality of recessed portions 19 is chlorinated polyolefin. By the chlorinated polyolefin having favorable adhesion property with polyolefin that is the syringe body 11 (base material) entering the recessed portion 19, the anchor effect is further increased.

According to an embodiment of the present invention, the printing layer 18 has an adjacent lamellar structure of chlorinated polypropylene adjacent to the outer surface 17 of the syringe body 11. Further, a total axial length of the adjacent lamellar structure of chlorinated polypropylene in the cross-section along the axis of the syringe body 11 is 10% or less of an axial length $d5$ of the printing layer 18 illustrated in FIG. 4. According to such an embodiment, because the lamellar structure of chlorinated polypropylene that weakens the adhesion strength between the outer surface 17 of the syringe body 11 and the printing layer 18 exists only in a very limited range, the adhesion strength between the outer surface 17 of the syringe body 11 and the printing layer 18 can be increased. The printing layer 18 may have a lamellar structure of chlorinated polypropylene at a position separate from the outer surface 17 of the syringe body 11, separately from the adjacent lamellar structure.

According to an embodiment of the present invention, the printing layer 18 has a body region separate from an outer edge of the printing layer 18 by 3 μm (see a length $d3$ of FIG. 4) or more in a direction along the outer surface 17 of the syringe body 11 and a thickness $d4$ of the printing layer 18 in the body region is 1 to 10 μm. With such a range, it can be said that the ink is printed at an intended position, and precision in indication becomes favorable. The thickness of the printing layer 18 in the body region is more preferably 2 to 8 μm.

According to an embodiment of the present invention, the outer surface 17 on which the printing layer 18 is printed is not compatible with the printing layer 18. By the outer surface 17 on which the printing layer 18 is printed being not compatible with the printing layer 18, the nature and physical property of the material of the syringe body 11 are not changed. Therefore, it is suppressed that a substance derived from the material of the syringe body 11 that is changed by compatibilization is melted in the medicine in the syringe body 11, or the strength of the syringe body 11 is decreased so that the syringe body 11 is easily broken or does not withstand high-pressure steam sterilization. Thus, according to an embodiment of the present invention, a clear interface is present between the outer surface 17 on which the printing layer 18 is printed and the printing layer 18.

According to an embodiment of the present invention, the printing layer 18 is formed by applying an ink to the outer surface 17 of the syringe body 11 made of polyolefin. Further, the ink has components including a volatile solvent, which contains a dissolving component dissolving the polyolefin, chlorinated polypropylene having a degree of chlorination in a range of 15 to 30%, a colorant, and a filler. Such an ink is also referred to as an ink of the present invention (or simply referred to as "ink") in the present specification.

(Chlorinated Polypropylene)

The ink of the present invention contains chlorinated polypropylene. Further, the degree of chlorination of the chlorinated polypropylene is in a range of 15 to 30%. In an embodiment of the present invention, the degree of chlorination is preferably in a range of 20 to 29%, more preferably in a range of 23 to 28%, and more preferably in a range of 25 to 27%. With such a range, the desired effects by the present invention can be efficiently provided. In addition, in an embodiment of the present invention, the degree of chlorination is 8.3 to 3.6% with respect to H in a propylene unit [—CH(CH$_3$)—CH$_2$-] in the chlorinated polypropylene. With such a range, it is possible to form the printing layer 18 that is less likely to be peeled off.

According to an embodiment of the present invention, an amount of the chlorinated polypropylene contained in the ink is preferably in a range of 10 to 35% by mass, more preferably in a range of 13 to 30% by mass, and further preferably in a range of 16 to 30% by mass. With such a range, it is possible to form the printing layer 18 that is less likely to be peeled off.

The chlorinated polypropylene that may be used in certain embodiments of the present invention may be synthesized with reference to a conventional known method, or if there is a commercially available product, the commercially available product may be purchased and prepared as the chlorinated polypropylene.

(Colorant)

The ink according to certain embodiments of the present invention contains a colorant. The color of the colorant is not particularly limited, but a black ink is used in the printing layer in many cases. As the black colorant that may be used in the ink of certain embodiments of the present invention, for example, carbon black such as furnace black, channel black, acetylene black, thermal black, or lampblack, a magnetic powder such as magnetite or ferrite, and the like are suitable. As for colorants of other colors, known colorants usable in the relevant field can be applied.

According to an embodiment of the present invention, an amount of colorant contained in the ink is preferably in a range of 3 to 15% by mass, and more preferably in a range of 5 to 10% by mass. With such a range, it is possible to form the printing layer 18 that is unlikely to be peeled off and easily visible.

(Filler)

The ink of the present invention contains a filler. By containing a filler, dispersibility of the ink is improved and glossiness can be controlled. Types of the filler are also not particularly limited, but the ink may contain, for example, an inorganic filler such as barium sulfate, talc, calcium carbonate, zinc carbonate, Wollastonite, silica, alumina, magnesium oxide, calcium silicate, sodium aluminate, calcium aluminate, sodium aluminosilicate, magnesium silicate, zinc oxide, antimony trioxide, zeolite, hydrotalcite, metallic fiber, metal whisker, ceramic whisker, potassium titanate, boron nitride, or carbon fiber; or an organic filler such as a naturally derived polymer such as starch, cellulose fine particles, or wood powder or modified products thereof. In particular, barium sulfate may function as an extender pigment and may also function as a stabilizer for preventing a dehydrochlorination reaction of chlorinated polypropylene.

According to an embodiment of the present invention, an amount of the filler contained in the ink is preferably in arrange of 15 to 60% by mass, more preferably in a range of 25 to 45% by mass, and further preferably in a range of 25 to 35% by mass. With such a range, it is possible to form the printing layer 18 that is unlikely to be peeled off and has less color unevenness.

(Volatile Solvent)

The ink of the present invention may contain a volatile solvent that contains a dissolving component dissolving the polyolefin.

According to an embodiment of the present invention, as the volatile solvent, for example, toluene, trimethylbenzene, cyclohexane, tetrahydrofuran, and the like are suitable. According to such an embodiment, the chlorinated polypropylene can be efficiently dissolved in the volatile solvent. Further, by combining toluene and trimethylbenzene, solubility of the chlorinated polypropylene can be further increased. Incidentally, trimethylbenzene is at least one kind of 1,2,4-trimethylbenzene, 1,2,3-trimethylbenzene, and 1,3,5-trimethylbenzene.

The volatile solvent contains a dissolving component dissolving the polyolefin. According to an embodiment of the present invention, the dissolving component is an aromatic hydrocarbon having a benzene ring structure and a hydrocarbon side chain and the number of carbon atoms of the hydrocarbon side chain is 2 or more. According to an embodiment of the present invention, the number of carbon atoms is preferably in a range of 2 to 10 and more preferably in a range of 2 to 5. With such a range, when the ink is applied to the outer surface 17 of the syringe body 11, the recessed portions 19 can be efficiently formed on the outer surface 17 of the syringe body 11. According to an embodiment of the present invention, as the dissolving component, p-cymene, ethylbenzene, and cumene are suitable, and particularly, p-cymene is preferred.

According to an embodiment of the present invention, an amount of the volatile solvent contained in the ink is preferably in a range of 15 to 40% by mass, more preferably in a range of 20 to 35% by mass, and further preferably in a range of 20 to 30% by mass (in the case of containing two or more kinds of volatile solvent, the total amount thereof). Further, according to an embodiment of the present invention, the ink preferably contains 15 to 40% by mass of toluene and more preferably contains 20 to 30% by mass of toluene. By containing toluene in such a range, the volatilization rate of the solvent when the ink is applied to the outer surface 17 of the syringe body 11 becomes appropriate, and as a result, it is suppressed that the lamellar structure of the chlorinated polypropylene is excessively formed in the printing layer. Further, a technical effect that the printing layer 18 can be formed without the syringe body 11 being substantially dissolved by toluene is obtained.

Further, according to an embodiment of the present invention, the printing layer 18 preferably contains 14 to 50% by mass of chlorinated polypropylene having a degree of chlorination in a range of 15 to 30%, and more preferably contains 18 to 43% by mass of chlorinated polypropylene having a degree of chlorination in a range of 15 to 30%. Further, according to an embodiment of the present invention, the printing layer 18 preferably contains 4 to 22% by mass of a colorant, and more preferably contains 7 to 14% by mass of a colorant. Further, according to an embodiment of the present invention, the printing layer 18 preferably contains 21 to 86% by mass of a filler, and more preferably contains 35 to 64% by mass of a filler.

According to an embodiment of the present invention, the outer surface 17 of the syringe body 11 is subjected to a sterilization treatment by an autoclave. According to certain embodiments of the present invention, because the recessed portion 19 of the syringe body 11 is filled with at least one kind of the components of the printing layer 18, peeling-off of the printing layer 18 is suppressed even when subjected to autoclave sterilization. The autoclave method will be described below.

The resin syringe 10 is a syringe before a medicine is filled. After the medicine is filled, by providing the cap 20 sealing the distal end opening of the syringe body 11 and the gasket 30 slidably disposed in the accommodating space 16 of the syringe body 11, the resin syringe 10 becomes the prefilled syringe 1. Thus, the prefilled syringe 1 includes the resin syringe 10, a medicine filled in the syringe body 11 of the resin syringe 10, the cap 20 sealing the distal end opening of the syringe body 11, and the gasket 30 slidably disposed in the syringe body 11. With such a prefilled syringe 1, because a label is not used, a case in which the label is peeled off does not occur, and a dosage of a medicine can be strictly controlled.

Further, in an embodiment of the present invention, the medicine is filled in the syringe body 11 in an amount more than a dose, and the printing layer 18 is a graduation line printed at a position where the internal capacity of the syringe body 11 coincides with the dose of the medicine. Because the printing layer 18 is formed directly on the outer surface 17 of the syringe body 11, deviation of the graduation line from an intended position is extremely reduced. Therefore, when the gasket is moved forward to the graduation line in order to make the amount of the medicine in the syringe body 11 coincide with the dose, the amount of the medicine in the syringe body 11 can be reliably made to coincide with the dose. Particularly, in the case of administration of a small dose of a medicine, that is, the dose of 0.5 mL or less, in order to more reliably make the amount of the medicine in the syringe body 11 when the gasket is moved forward to the graduation line coincide with the dose, accuracy of the position of the graduation line is extremely important.

[Method for Producing Resin Syringe]

Figure 5:
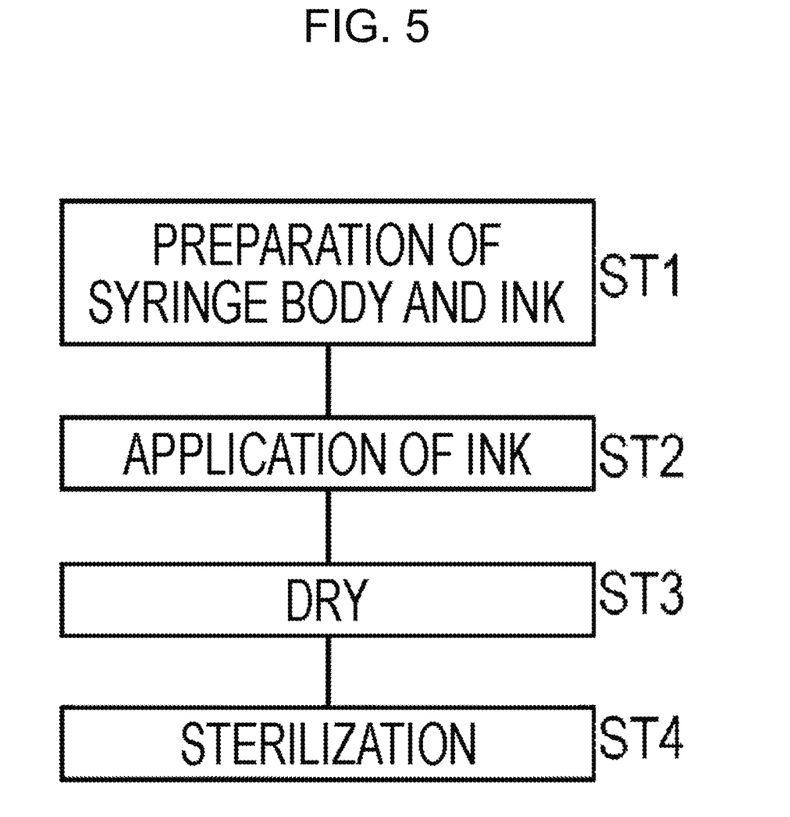
FIG. 5 is a flowchart illustrating a method for producing a resin syringe according to an embodiment of the present invention.

Next, a method for producing the resin syringe 10 according to this embodiment will be described. FIG. 5 is a flowchart illustrating a method for producing a resin syringe according to an embodiment of the present invention. In the method, the syringe body 11 made of polyolefin is prepared as illustrated in FIG. 5. Further, an ink having components including a volatile solvent, which contains a dissolving component dissolving the polyolefin, chlorinated polypropylene having a degree of chlorination in a range of 15 to 30%, a colorant, and a filler is prepared (preparation step (ST1)). Next, the ink is applied to at least a part of the outer surface 17 of the syringe body 11 (application step (ST2)). Next, the applied ink is dried to form the printing layer 18 having components including the chlorinated polypropylene, the colorant, and the filler on the outer surface 17 (drying step (ST3)). In the application step, by dissolving at least a part of the outer surface 17 by the dissolving component, the plurality of recessed portions 19 are formed on the outer surface 17 and each of the plurality of recessed portions 19 is filled with at least one kind of components of the ink. Further, by drying the ink, each of the plurality of recessed portions 19 is filled with at least one kind of the components of the printing layer 18.

<Preparation Step>

In the method for producing the resin syringe 10 of the present invention, the syringe body 11 made of polyolefin is prepared. Further, the method includes a preparation step of preparing an ink having components including a volatile solvent, which contains a dissolving component dissolving the polyolefin, chlorinated polypropylene having a degree of chlorination in a range of 15 to 30%, a colorant, and a filler (see ST1 of FIG. 5).

As for the syringe body 11 made of polyolefin, a commercially available product can be purchased and prepared as described above. The ink can be prepared by appropriately mixing the components constituting the ink described above.

<Application Step and Drying Step>

The method for producing a resin syringe of the present invention includes an application step of applying the ink to at least a part of the outer surface 17 of the syringe body 11 (see ST2 of FIG. 5). Further, the method for producing a resin syringe of the present invention includes a drying step of forming the printing layer 18 having components including the colorant and the filler (see ST3 of FIG. 5).

The application step is sufficient that an amount enough to print the printing layer 18 can be applied, and the application amount can be appropriately set according to a printing area of the printing layer 18. In a case in which the printing layer 18 is graduation indicating the internal capacity of the syringe body 11, it is preferable to apply the ink such that the ink becomes a linear graduation line along the circumferential direction of the syringe body 11. The thickness of the graduation line is preferably 0.1 to 1.0 mm and more preferably 0.3 to 0.6 mm. Incidentally, only one graduation line may be provided as a gauge line indicating a dose of a medicine on the outer surface 17 of the syringe body 11. Further, a plurality of graduation lines may be intermittently provided to indicate a plurality of internal capacities of the syringe body 11. Further, a specific application method in the application step is also not particularly limited, and for example, it is suitable to use screen printing, offset printing, and the like.

Further, the dying condition in the drying step is also not particularly limited and is sufficient to be a condition that the volatile solvent in the ink is substantially volatilized, but the drying step is preferably performed, for example, at 60° C. for 30 minutes. In addition, the ink may be dried using a halogen lamp or the like at a higher temperature in a short period of time.

In the method for producing the resin syringe 10 of the present invention, in the application step, by dissolving at least a part of the outer surface 17 by the dissolving component, the plurality of recessed portions 19 are formed on the outer surface 17 and each of the plurality of recessed portions 19 is filled with at least one kind of components of the ink. Further, by drying the ink, each of the plurality of recessed portions 19 is filled with at least one kind of the components of the printing layer 18. In this way, the resin syringe 10 in which the printing layer 18 is printed on at least a part of the outer surface 17 of the syringe body 11 made of polyolefin as illustrated in FIGS. 2 to 4 can be produced. The printing layer 18 in the resin syringe 10 contains components including chlorinated polypropylene having a degree of chlorination in a range of 15 to 30%, a colorant, and a filler. The outer surface 17 on which the printing layer 18 is printed has the plurality of recessed portions 19. Each of the plurality of recessed portions 19 has a depth d1 of 50 nm or more and less than 1 µm and a width d2 of 50 nm or more and less than 1 µm. Each of the plurality of recessed portions 19 is filled with at least one kind of the components of the printing layer 18.

Further, in an embodiment of the present invention, a method for producing the resin syringe 10 is provided. In the method, the syringe body 11 made of polyolefin is prepared, and an ink having components including a volatile solvent, which contains a dissolving component dissolving the polyolefin, chlorinated polypropylene having a degree of chlorination in a range of 15 to 30%, a colorant, and a filler is prepared. Further, the ink is applied to the outer surface 17 of the syringe body 11. Further, the applied ink is dried to form the printing layer 18 having components including chlorinated polypropylene, a colorant, and a filler on the outer surface 17. In the application step, by dissolving at least a part of the outer surface 17 by the dissolving component, the plurality of recessed portions 19 are formed on the outer surface 17. Further, each of the plurality of recessed portions 19 is filled with at least one kind of the components of the ink. Further, in the drying of the ink, by volatilizing the volatile solvent in the ink components, each of the plurality of recessed portions 19 is filled with at least one kind of the components of the printing layer 18.

<Autoclave Sterilization Step>

In an embodiment of the present invention, an empty syringe for filling a medicine such as a prefillable syringe has to be in a clean and antiseptic state until the medicine is filled, and thus the syringe may be subjected to a sterilization treatment in a state of being accommodated in a packaging material in advance. Therefore, according to an embodiment of the present invention, the method includes a sterilization step of subjecting the syringe body 11 to autoclave sterilization (see ST4 of FIG. 5).

According to an embodiment of the present invention, the autoclave sterilization is carried out at preferably 121 to 125° C. and more preferably 121 to 123° C. Further, according to an embodiment of the present invention, the autoclave sterilization is performed for preferably 20 to 120 minutes, more preferably 20 to 90 minutes, and further preferably 20 to 60 minutes.

EXAMPLES

Hereinafter, representative embodiments of the present invention will be described and the present invention will be further described; however, as a matter of course, the present invention is not limited to these embodiments. Incidentally, "part(s)" represents "part(s) by mass" and "%" represents "% by mass" in Examples unless specifically noted. In addition, operations and measurement of physical properties or the like were carried out under the conditions of at room temperature (20 to 25° C.)/relative humidity of 40 to 50% RH unless specifically noted.

Example 1

An ink was applied to one place of the outer surface 17 of the syringe body 11 of a cyclo olefin polymer (ZEONEX (registered trademark) manufactured by Zeon Corporation) such that the ink became a linear graduation line annularly continued in a circumferential direction of the syringe body 11. Specifically, while the syringe body 11 was rotated about the axis, an ink prepared by the following method was applied using a screen printer for a curved face (SK-250-S type) manufactured by Shinei Kogyo Co., Ltd. Thereafter, the ink was dried at 60° C. for 30 minutes to produce the resin syringe 10 having a gauge line indicating a dose of a medicine.

(Preparation of Ink)

An ink having components including 26 parts of toluene, 6.5 parts of trimethylbenzene, 2 parts of naphthalene, 8 parts of carbon black, 20 parts of chlorinated polypropylene having a degree of chlorination of 26% (HARDLEN (registered trademark) (13-LLP) manufactured by TOYOBO CO., LTD.), 0.5 parts of p-cymene, and 37 parts of barium sulfate was prepared by mixing the respective components.

Comparative Example 1

The resin syringe 10 was produced in the same manner as in Example 1, except that preparation of an ink was performed as follows.

(Preparation of Ink)

An ink having components including 29 parts of toluene, 6.5 parts of trimethylbenzene, 1.5 parts of naphthalene, 2 parts of methanol, 0.5 parts of isobutanol, 8 parts of carbon black, 20 parts of chlorinated polyethylene having a degree of chlorination of 22 to 25% (ELASLEN (registered trademark) (grade: 252B) manufactured by Showa Denko K.K.), and 32.5 parts of barium sulfate was prepared by mixing the respective components.

<Evaluation>

(Observation of Interface)

The resin syringes 10 having the printing layer 18 printed thereon, which were produced in Example 1 and Comparative Example 1, were coated with platinum and embedded in resin by Luft method. Thereafter, ultrathin sections (syringe sections) were produced along the axis of the syringe body 11.

Figure 6:
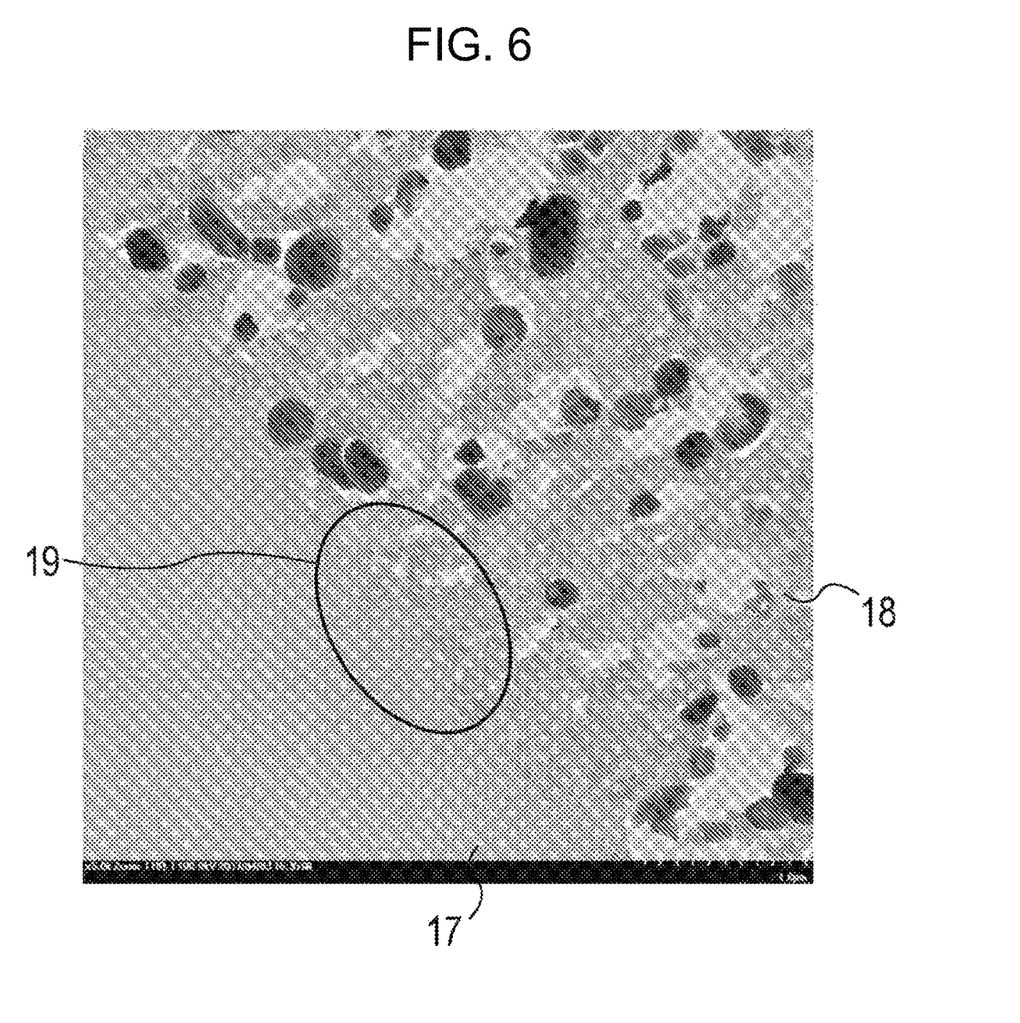
FIG. 6 is a TEM image (magnification: 5000 times) of Example 1 constituting an experimental example of the present invention.
Figure 7:
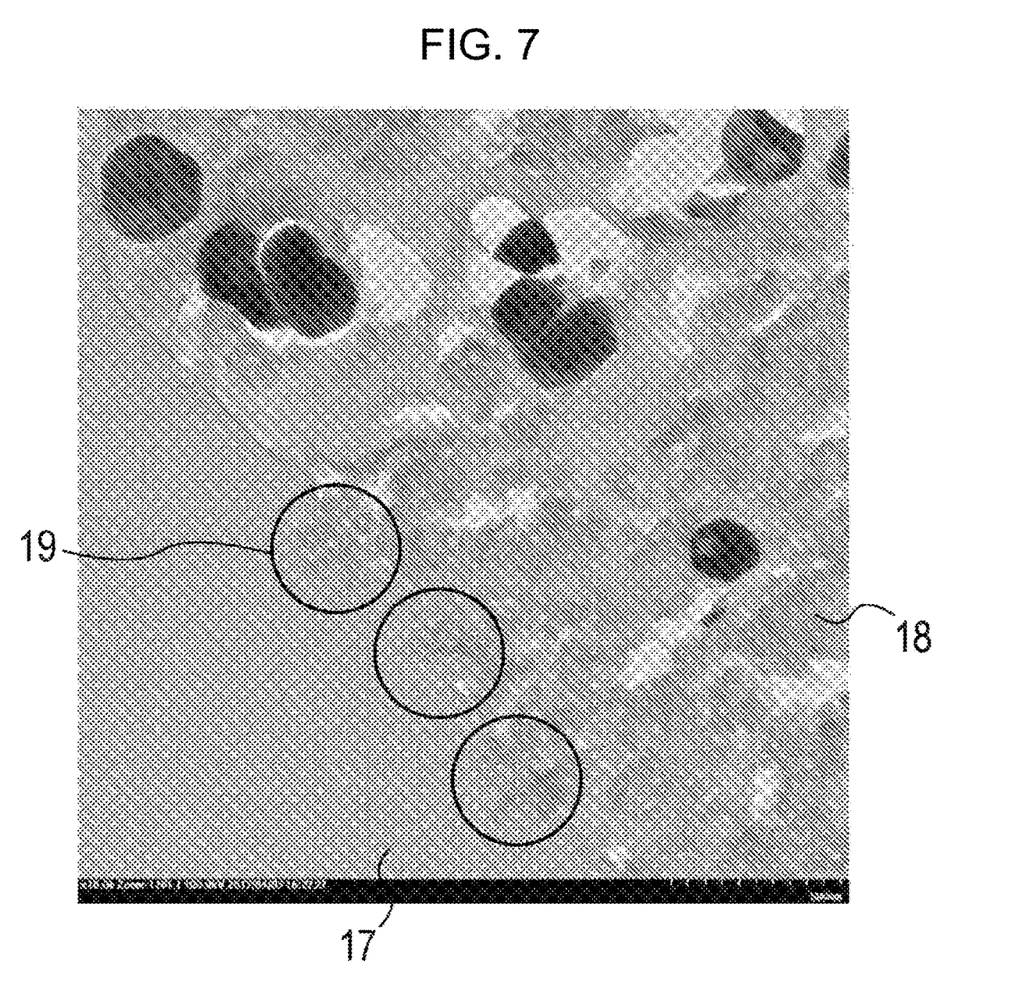
FIG. 7 is a TEM image (magnification: 10000 times) of Example 1.
Figure 8:
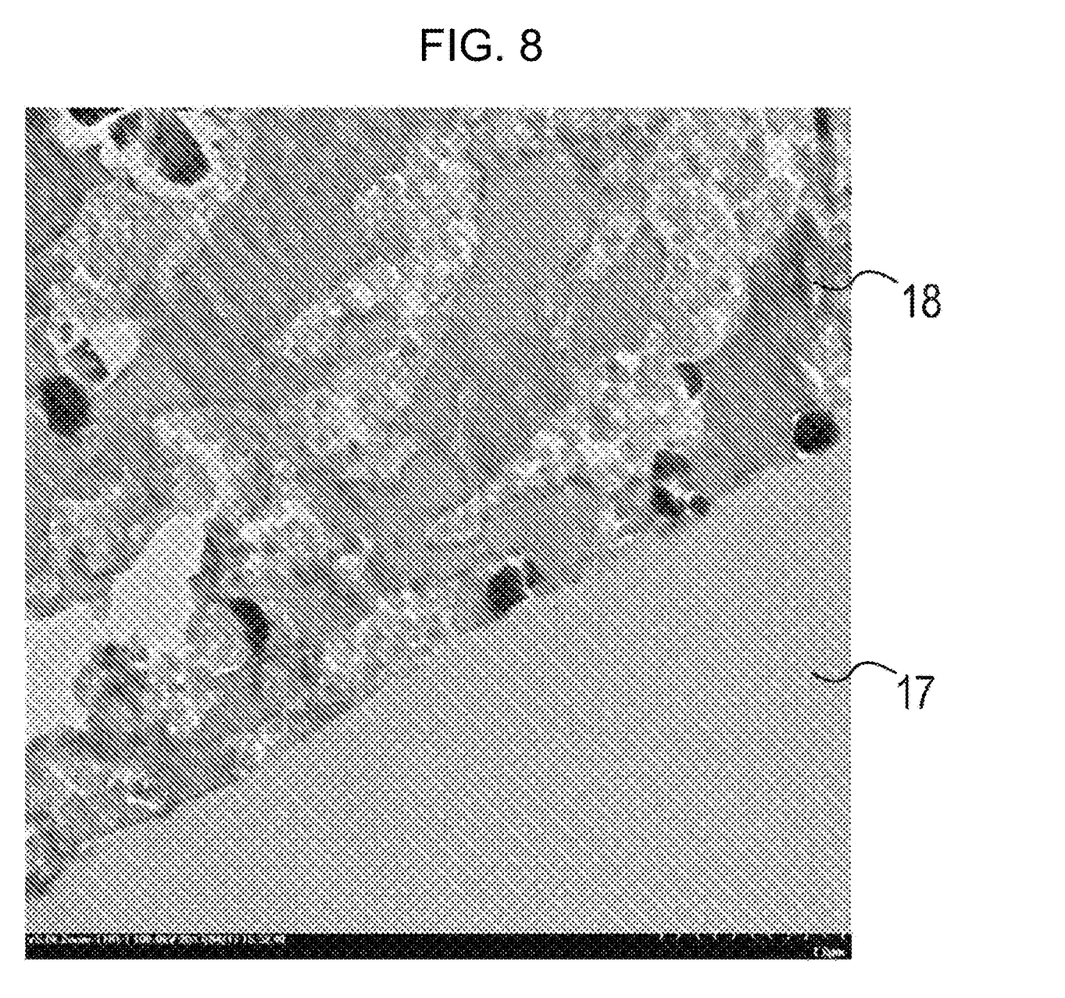
FIG. 8 is a TEM image (magnification: 5000 times) of Comparative Example 1.
Figure 9:
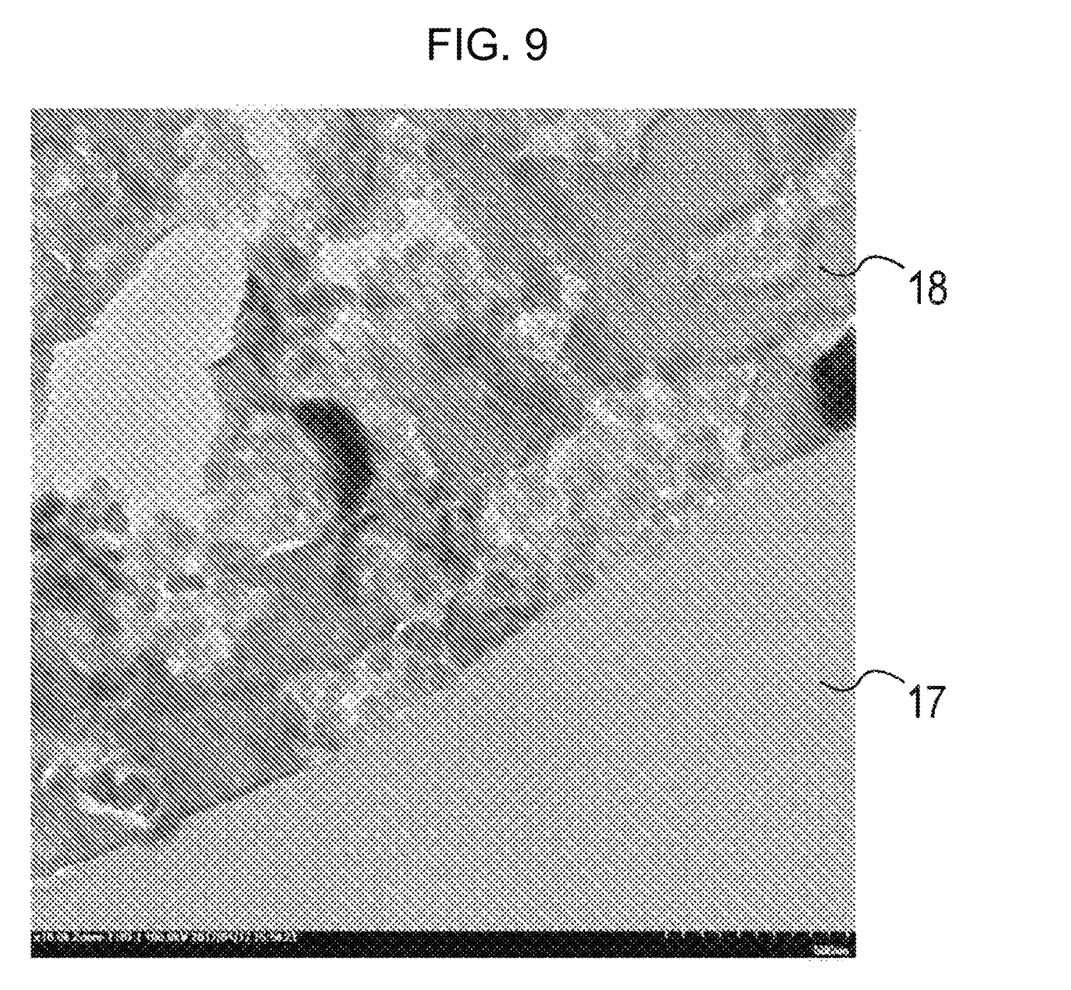
FIG. 9 is a TEM image (magnification: 10000 times) of Comparative Example 1.

The outer surfaces of the syringe sections were observed using a transmission electron microscope (TEM) in a bright field (magnification: 5000 times, 10000 times) The observed TEM images are shown in FIG. 6 (Example 1: 5000 times), FIG. 7 (Example 1: 10000 times), FIG. 8 (Comparative Example 1: 5000 times), and FIG. 9 (Comparative Example 1: 10000 times). In FIGS. 6 and 7, the plurality of recessed portions 19 are observed to enter the syringe body 11 at the interface between the printing layer 18 and the outer surface 17 of the syringe body 11. Further, as shown in FIG. 7, it is found that at least one kind of the ink components (particularly, chlorinated polyolefin shown in pale black) is filled in the recessed portion 19. On the other hand, as shown in FIGS. 8 and 9, in Comparative Example 1, there was no place in which the recessed portion 19 can be recognized at the interface between the printing layer 18 and the outer surface 17 of the syringe body 11. The reason for this is considered that the ink used in Comparative Example 1 does not contain a dissolving component dissolving polyolefin.

Incidentally, white particles having a size of about several hundred nm or minute white particles observed in the printing layer 18 are barium sulfate, and aggregates of gray particles having a size of about 30 to 50 nm observed in the printing layer 18 are carbon black.

(Element Distribution Observation)

The element distribution of the syringe section of Example 1 was observed using an energy dispersive X-ray spectroscopy. As a result, chlorine was not observed in the syringe body. Because chlorine is derived from chlorinated polypropylene, that is, it is suggested that the outer surface 17 on which the printing layer 18 is printed is not compatible with the printing layer 18. In other words, it can be said that a clear interface is formed between the outer surface 17 on which the printing layer 18 is printed and the printing layer 18.

(Measurement of Size of Recessed Portion)

Regarding all of cases where the recessed portion 19 can be clearly recognized in images captured at 10 places randomly selected in syringe sections of Example 1, the maximum width and the maximum depth thereof were measured with reference to a scale bar. As a result, the depth d1 and the width d2 (see FIG. 4) of the recessed portion 19 in Example 1 were in ranges of 50 to 150 nm and 50 to 200 nm, respectively.

(Thickness of Printing Layer)

Figure 10:
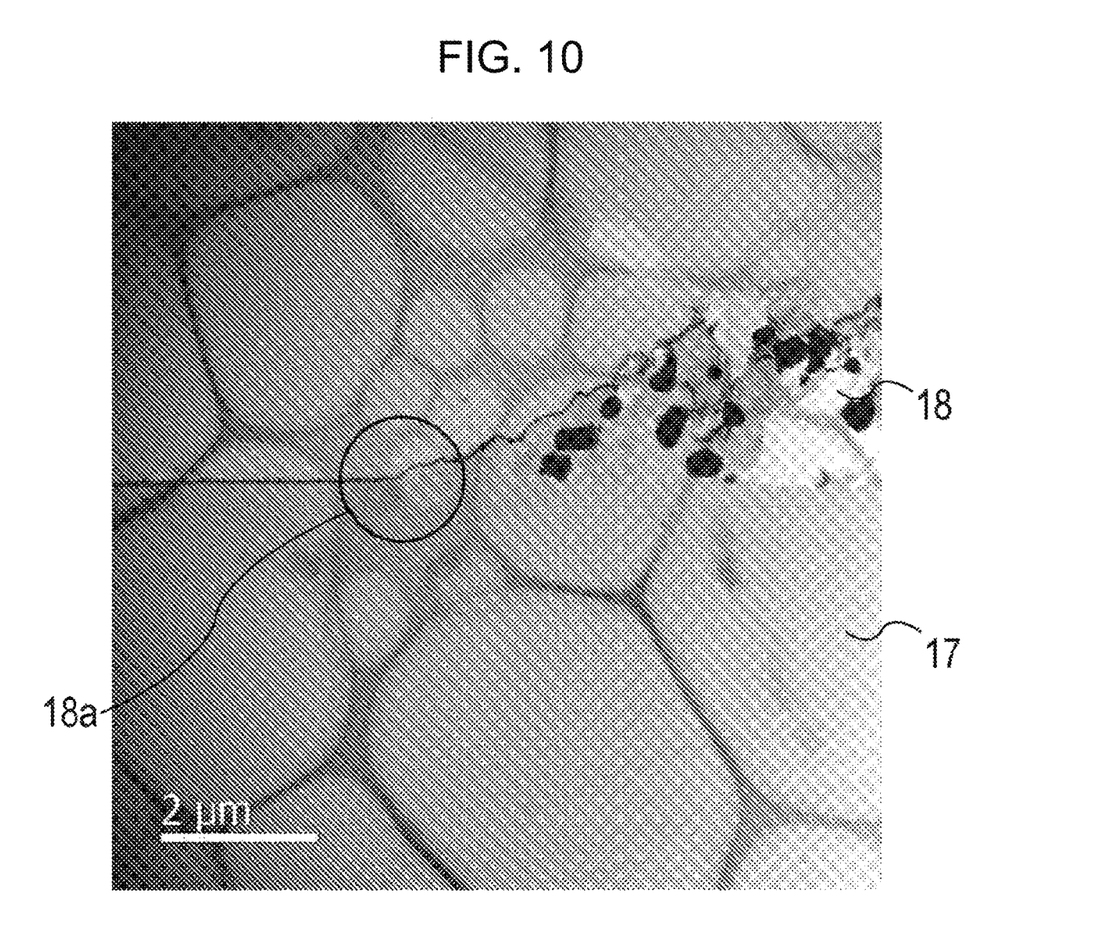
FIG. 10 is a TEM image (magnification: 2000 times) of Example 1.
Figure 11:
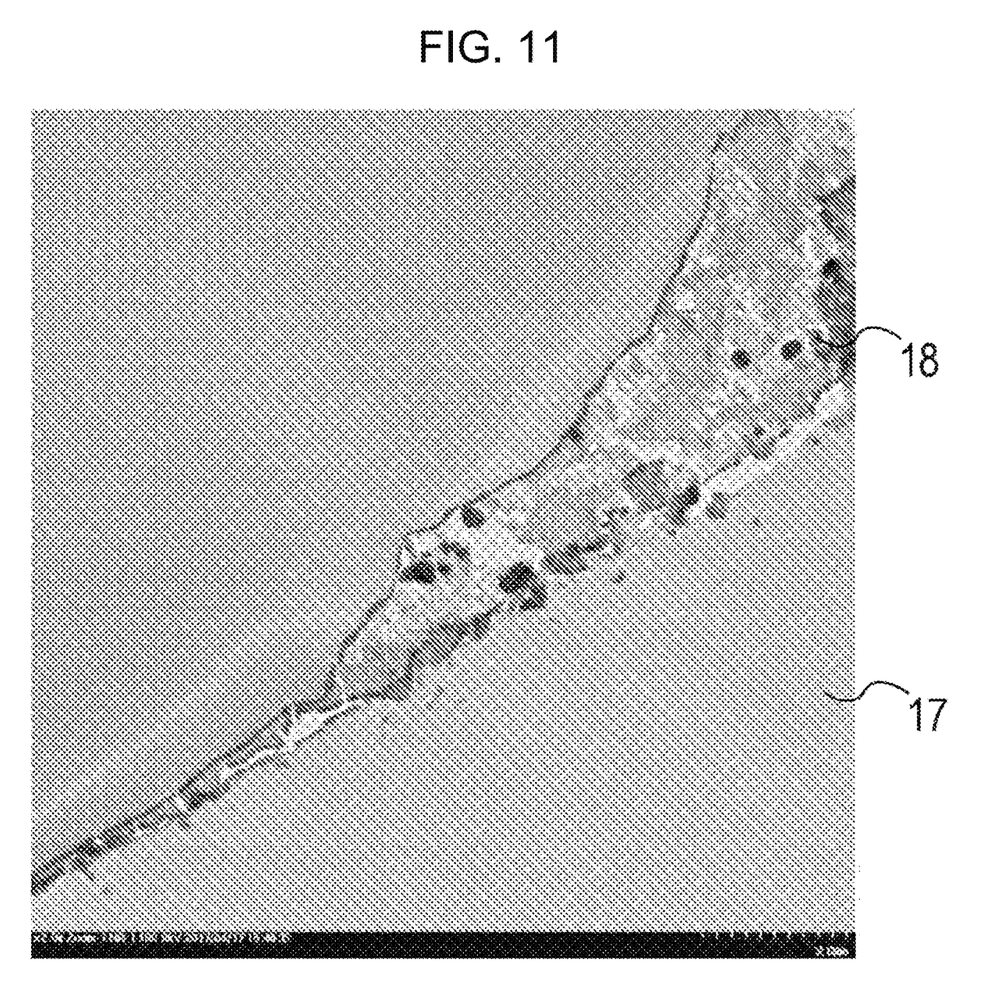
FIG. 11 is a TEM image (magnification: 2000 times) of Comparative Example 1.

FIG. 10 and FIG. 11 are TEM images captured in the same manner as described above at a magnification of 2000 times of Example 1 and Comparative Example 1, respectively. In FIGS. 4 and 10, in Example 1, the thickness d4 of the printing layer 18 at a portion separate from the outer edge 18a of the printing layer 18 by 3 μm (see the length d3 of FIG. 4) was 1.5 μm. Further, in FIG. 11, in Comparative Example 1, the thickness d4 of the printing layer 18 also at a portion separate from the edge of the printing layer 18 (in FIG. 11, the edge is present at the further lower left side) by 3 μm was less than 1 μm.

(Peeling Test)

A peeling test was performed with reference to JIS K5600-5-6:1999 (I2409:1992). Specifically, CELLOTAPE (registered trademark) CT-18 was strongly bonded by pressure to stride over a printing part along the axis of the syringe body and the edge of the tape was peeled off at once at an angle of 60°. As a result, clear peeling was not recognized in Example 1, but partial peeling-off of the tape was recognized in Comparative Example 1.

REFERENCE NUMERAL LIST

1 Prefilled Syringe
10 Resin Syringe
11 Syringe Body
17 Outer Surface
18 Printing Layer
20 Cap (Sealing Member)
30 Gasket
40 Plunger
d1 Depth (of Recessed Portion)
d2 Width (of Recessed Portion)
d3 Length (of Printing Layer from Outer Edge in Axial Direction)
d4 Thickness (of Printing Layer at Position Separate From Outer Edge By Length d3)
d5 Axial Length (of Printing Layer)

The invention claimed is:

1. A resin syringe comprising:
a syringe body made of polyolefin, and
a printing layer having a shape that extends in a band around an outer surface of the syringe body,
wherein the printing layer comprises components including chlorinated polypropylene having a degree of chlorination in a range of 15 to 30%, a colorant, and a filler,
wherein a plurality of recessed portions is formed in the outer surface of the syringe body on which the printing layer is printed and the plurality of recessed portions form a shape that extends in a band around the outer surface of the syringe body and that is entirely covered by the printing layer,
wherein each of the plurality of recessed portions has a depth of 50 nm or more and less than 1 μm and a width of 50 nm or more and less than 1 μm and is filled with at least one of the components of the printing layer, and
wherein regions of the outer surface of the syringe body that are distal and proximal of the printing layer are free of recessed portions.

2. The resin syringe according to claim 1, wherein the printing layer is a graduation line indicating an internal capacity of the syringe body.

3. The resin syringe according to claim 1, wherein the depth of each of the plurality of recessed portions is in a range of 50 to 200 nm.

4. The resin syringe according to claim 1, wherein the width of each of the plurality of recessed portions is in a range of 100 to 500 nm.

5. The resin syringe according to claim 1, wherein the printing layer has a body region separate from an outer edge of the printing layer by 3 μm or more in a direction along the outer surface of the syringe body, and a thickness of the printing layer in the body region is in a range of 1 to 10 μm.

6. The resin syringe according to claim 1, wherein the outer surface on which the printing layer is printed is not compatible with the printing layer.

7. The resin syringe according to claim 1, wherein the resin syringe is a syringe that has been subjected to autoclave sterilization.

8. The resin syringe according to claim 1, wherein an amount of the chlorinated polypropylene in the printing layer is in a range of 10 to 35% by mass.

9. The resin syringe according to claim 1, wherein an amount of the colorant in the printing layer is in a range of 3 to 15% by mass.

10. The resin syringe according to claim 1, wherein an amount of the filler in the printing layer is in a range of 15 to 60% by mass.

11. The resin syringe according to claim 1, wherein at least one of the components of the printing layer filled in each of the plurality of recessed portions comprises 15 to 40% by mass of toluene.

12. The resin syringe according to claim 1, wherein at least one of the components of the printing layer filled in each of the plurality of recessed portions comprises chlorinated polyolefin.

13. The resin syringe according to claim 1, wherein the polyolefin is a cyclo olefin polymer, a cyclo olefin copolymer, or polypropylene.

14. The resin syringe according to claim 1, wherein the resin syringe comprises a prefilled syringe.

15. The resin syringe according to claim 1, wherein the filler comprises barium sulfate.

16. The resin syringe according to claim 1, wherein the syringe body is configured to be filled with medicine in an amount more than a dose of the medicine.

17. The resin syringe according to claim 16, wherein the printing layer is a graduation line printed at a position where an internal capacity of the syringe body coincides with the dose of the medicine.

18. The resin syringe according to claim 1, wherein the syringe body comprises a cylindrical shape.

19. The resin syringe according to claim 1, wherein at least one of the components of the printing layer filled in each of the plurality of recessed portions comprises a dissolving component.

20. The resin syringe according to claim 1, wherein at least one of the components of the printing layer filled in each of the plurality of recessed portions comprises black colored ink.

* * * * *